United States Patent
Swanson et al.

(10) Patent No.: US 10,234,412 B2
(45) Date of Patent: Mar. 19, 2019

(54) IDENTIFICATION OF COMBUSTIBLE GAS SPECIES VIA PULSED OPERATION OF A COMBUSTIBLE GAS SENSOR

(71) Applicant: MSA TECHNOLOGY, LLC, Cranberry Township, PA (US)

(72) Inventors: Meghan E. Swanson, Pittsburgh, PA (US); Michael Alvin Brown, Cranberry Township, PA (US)

(73) Assignee: MSA TECHNOLOGY, LLC, Cranberry Township, PA (US)

( * ) Notice: Subject to any disclaimer, the term of this patent is extended or adjusted under 35 U.S.C. 154(b) by 152 days.

(21) Appl. No.: 15/343,956

(22) Filed: Nov. 4, 2016

(65) Prior Publication Data

US 2018/0128763 A1 May 10, 2018

(51) Int. Cl.
*G01N 27/16* (2006.01)
*G01N 31/10* (2006.01)
(Continued)

(52) U.S. Cl.
CPC ............. *G01N 27/16* (2013.01); *F01N 11/00* (2013.01); *G01N 27/407* (2013.01); *G01N 31/10* (2013.01);
(Continued)

(58) Field of Classification Search
CPC ........ G01N 27/16; G01N 31/10; G01N 31/12; G01N 27/124; G01N 25/4873; G01N 27/407; F01N 11/00; G01M 15/102
See application file for complete search history.

(56) References Cited

U.S. PATENT DOCUMENTS

| 3,948,810 A | 4/1976 | Hervert |
| 4,097,353 A | 6/1978 | Kishida |
| (Continued) | | |

FOREIGN PATENT DOCUMENTS

| EP | 0094863 | 11/1983 |
| EP | 0130785 | 3/1988 |
| (Continued) | | |

OTHER PUBLICATIONS

Written Opinion and International Search Report corresponding to counterpart PCT International patent application No. PCT/US2017/056716.

(Continued)

*Primary Examiner* — Jennifer Wecker
(74) *Attorney, Agent, or Firm* — Bartony & Associates, LLC

(57) ABSTRACT

A combustible gas sensor includes a first sensing element, which includes a catalyst and a heating element in operative connection with the catalyst to heat the catalyst above a temperature to combust gas analytes of interest, and electronic circuitry in operative connection with the heating element of the first sensing element to periodically cycle the first sensing element between a temperature above the temperature to combust the analytes of interest and a temperature at which the catalyst is substantially inactive to catalyze oxidative combustion of the analytes of interest. The electronic circuitry is adapted to determine a species of at least one of the gas analytes of interest from a first output of the combustible gas sensor during an ON time within a cycle duration. The electronic circuitry is further adapted to determine a concentration of the species of gas from a second output of the combustible gas sensor.

25 Claims, 8 Drawing Sheets

(51) Int. Cl.
  *G01N 31/12* (2006.01)
  *G01N 27/407* (2006.01)
  *F01N 11/00* (2006.01)
  *G01N 25/20* (2006.01)
  *G01M 15/10* (2006.01)
  *G01N 25/48* (2006.01)
  *G01N 27/12* (2006.01)

(52) U.S. Cl.
  CPC ........... *G01N 31/12* (2013.01); *G01M 15/102* (2013.01); *G01N 25/4873* (2013.01); *G01N 27/124* (2013.01)

(56) References Cited

U.S. PATENT DOCUMENTS

| | | | |
|---|---|---|---|
| 4,280,845 A | 7/1981 | Matsushisa | |
| 4,533,520 A | 8/1985 | Bossart | |
| 4,569,826 A | 2/1986 | Shiratori | |
| 4,627,269 A * | 12/1986 | Forster | G01N 27/124 73/1.05 |
| 4,950,628 A | 8/1990 | Landon | |
| 5,234,837 A | 8/1993 | Accorsi | |
| 5,368,713 A | 11/1994 | Friese | |
| 5,401,470 A | 3/1995 | Poli | |
| 5,423,973 A | 6/1995 | Friese | |
| 5,494,701 A | 2/1996 | Clough | |
| 5,528,225 A | 6/1996 | Sakai | |
| 5,565,634 A | 10/1996 | Graessle | |
| 5,599,584 A | 2/1997 | Champney, Jr. | |
| 5,780,715 A | 7/1998 | Imblum | |
| 5,841,021 A | 11/1998 | De Castro | |
| 5,902,556 A | 5/1999 | Van De Vyver | |
| 6,019,946 A | 2/2000 | Castillo | |
| 6,071,476 A | 6/2000 | Young | |
| 6,080,219 A | 6/2000 | Jha | |
| 6,131,438 A | 10/2000 | Zanini-Fisher | |
| 6,344,174 B1 | 2/2002 | Miller | |
| 6,548,024 B1 | 4/2003 | Doncaster | |
| 6,663,834 B1 | 12/2003 | Miller | |
| 6,705,152 B2 | 3/2004 | Routkevitch | |
| 6,756,016 B2 | 6/2004 | Miller | |
| 6,812,708 B2 | 11/2004 | Bristol | |
| 7,559,228 B2 | 7/2009 | Baha | |
| 8,826,721 B2 | 11/2014 | Zanella, Sr. | |
| 9,228,967 B2 | 1/2016 | Alepee | |
| 2004/0208789 A1 | 10/2004 | Miller | |
| 2005/0217370 A1 | 10/2005 | Takahashi | |
| 2005/0220672 A1 * | 10/2005 | Takahashi | G01N 27/16 422/94 |
| 2006/0228261 A1 | 10/2006 | Iwamoto | |
| 2008/0140301 A1 * | 6/2008 | Ding | G01N 27/407 701/115 |
| 2013/0186777 A1 * | 7/2013 | Scheffler | G01N 27/26 205/785.5 |
| 2015/0212030 A1 * | 7/2015 | Alepee | G01N 27/128 436/141 |

FOREIGN PATENT DOCUMENTS

| | | |
|---|---|---|
| EP | 0311964 | 4/1989 |
| EP | 0313390 | 4/1989 |
| EP | 0364982 A2 | 4/1990 |
| EP | 0419282 | 3/1991 |
| EP | 0703449 | 3/1996 |
| EP | 0500598 B1 | 3/1997 |
| EP | 1505385 A1 | 2/2005 |
| GB | 2067294 | 7/1981 |
| GB | 2121180 | 12/1983 |
| JP | H08247984 | 9/1996 |
| JP | 2008096267 | 4/2008 |
| WO | WO2000043765 A1 | 7/2000 |
| WO | WO2006111727 A1 | 10/2006 |
| WO | WO2011053866 A1 | 5/2011 |
| WO | WO2018085026 | 5/2018 |

OTHER PUBLICATIONS

Mosely, P.T., Solid State Gas Sensors, Adams Hilger Press, Bristol, England, 18-31 (1987).

Firth, J.G. et al., The Principles of the Detection of Flammable Atmospheres by Catalytic Devices, Combustion and Flame 21, 303-311 (1973).

Cullis, C.F., Eds., Detection and Measurement of Hazardous Gases, Heinemann, Exeter, 29-67 (1981).

* cited by examiner

IDENTIFICATION OF COMBUSTIBLE GAS SPECIES VIA PULSED OPERATION OF A COMBUSTIBLE GAS SENSOR

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Catalytic or combustible (flammable) gas sensors have been in use for many years to, for example, prevent accidents caused by the explosion of combustible or flammable gases. In general, combustible gas sensors operate by catalytic oxidation of combustible gases. As illustrated in FIGS. 1A and 1B, a conventional combustible gas sensor 10 typically includes an element such as a platinum element wire or coil 20 encased in a refractory (for example, alumina) bead 30, which is impregnated with a catalyst to form an active or sensing element, which is sometimes referred to as a pelement 40, pellistor, detector or sensing element. A detailed discussion of pelements and catalytic combustible gas sensors which include such pelements is found in Mosely, P. T. and Tofield, B. C., ed., *Solid State Gas Sensors*, Adams Hilger Press, Bristol, England (1987). Combustible gas sensors are also discussed generally in Firth, J. G. et al., *Combustion and Flame* 21, 303 (1973) and in Cullis, C. F., and Firth, J. G., Eds., *Detection and Measurement of Hazardous Gases*, Heinemann, Exeter, 29 (1981).

Bead 30 will react to phenomena other than catalytic oxidation that can change its output (i.e., anything that changes the energy balance on the bead) and thereby create errors in the measurement of combustible gas concentration. Among these phenomena are changes in ambient temperature, humidity and pressure.

To minimize the impact of secondary effects on sensor output, the rate of oxidation of the combustible gas may be measured in terms of the variation in resistance of sensing element or pelement 40 relative to a reference resistance embodied in an inactive, compensating element or pelement 50. The two resistances are typically part of a measurement circuit such as a Wheatstone bridge circuit as illustrated in FIG. 1B. The output or the voltage developed across the bridge circuit when a combustible gas is present provides a measure of the concentration of the combustible gas. The characteristics of compensating pelement 50 are typically matched as closely as possible with active or sensing pelement 40. Compensating pelement 50, however, typically either carries no catalyst or carries an inactivated/poisoned catalyst.

Active or sensing pelement 40 and compensating pelement 50 can, for example, be deployed within wells 60a and 60b of an explosion-proof housing 70 and can be separated from the surrounding environment by a flashback arrestor, for example, a porous metal frit 80. Porous metal frit 80 allows ambient gases to pass into housing 70 but prevents ignition of flammable gas in the surrounding environment by the hot elements. Such catalytic gas sensors are usually mounted in instruments which, in some cases, must be portable and, therefore, carry their own power supply. It is, therefore, desirable to minimize the power consumption of a catalytic gas sensor.

The operation of a catalytic combustible gas sensor proceeds through electrical detection of the heat of reaction of a combustible gas on the oxidation catalyst, usually through a resistance change via a Wheatstone bridge as described above. The oxidation catalysts may, for example, operate in the temperature range of 350-600° C. for methane detection. The sensor must sufficiently heat the pelement through resistive heating. Generally the heating and detecting element (element 20) are one and the same. A platinum alloy is often used because of its large temperature coefficient of resistance, resulting in a large signal in target or analyte gas.

As described above, the heating element may be a helical coil of fine wire. The heating element can also be a planar meander formed into a hotplate or other similar physical form. The catalyst being heated often includes an active metal catalyst dispersed upon a refractory catalyst substrate. Usually the active metal is one or more noble metals such as palladium, platinum, rhodium, silver, and the like and the refractory metal oxide support consists of one or more oxides of aluminum, zirconium, titanium, silicon, cerium, tin, lanthanum and the like, which may or may not have high surface area greater than 75 $m^2/g$. The support and catalytic metal precursor may be adhered to the heating element in one step or in separate steps using thick film or ceramic slurry techniques as known in the art. Often, a catalytic metal salt precursor is heated during manufacture to decompose it to the desired dispersed active metal, metal alloy, and/or metal oxide.

Oxidation catalysts formed onto a helical wire heater are typically referred to as pelements while those formed onto hotplates (whether microelectronic mechanical systems (MEMS) hotplates or conventional, larger hotplates) are sometimes known by the substrate. Oxidative catalysts formed on MEMS heating elements are sometimes referred to herein as MEMS pellistors. As described above, the detecting pelements or catalytically active hotplates can be paired with a similarly sized heater coated with materials with similar thermal conductivity as the active catalyst but without active sites. The inactive pelement or hotplate may be used to compensate for changes in ambient temperature, relative humidity, or background thermal conductivity not associated with a combustible gas and are therefore often referred to as compensators. The matched pair of detecting and compensating elements can be assembled in a Wheatstone bridge configuration for operation and combustible gas detection, which requires that both the detector and compensator operate at the same elevated temperature. Alternately, the compensator function can be achieved by using a detecting pelement or hotplate that is operated well below the minimum oxidation temperature using an electronically controlled independent bridge circuit as taught in U.S. Pat. No. 8,826,721. Advantages of the independent bridge circuit operating mode include power savings and longer life due to switching active detector pelements or hotplates.

It is well known that oxidation catalysts can suffer deactivation as a result of catalyst poisons and inhibitors such as compounds containing silicone, sulfur, phosphorus, and lead which make their way to the catalyst from the gas phase but become bound to the solid catalyst surface. To ameliorate the effects of environmental poisons, catalytic combustible sensors may include filtration material(s) upstream of the active catalyst to trap inhibiting or poisoning compounds. Such filters may, for example, rely on the actions of physisorption, chemisorption, chemical reaction, or a combination thereof to increase the span, stability and lifetime of the combustible sensor. Filters may, for example, include a variety of metal salts, activated carbon, adsorbent metal oxides or combinations thereof which have been found to reduce the effective concentration of poisons reaching the catalyst. See, for example, U.S. Pat. No. 6,756,016. A consequence of adding upstream filtration to combustible sensors is that span and response time may be reduced for combustible gases of interest (particularly, for heavy hydrocarbons when adsorbents with a surface area greater than 75 m²/g are employed or thick filters are used). Upstream filtration is not limited to external filters and may include materials coated directly onto the catalyst surface.

SUMMARY

In one aspect, a combustible gas sensor includes a first sensing element, which includes a catalyst and a heating element in operative connection with the catalyst to heat the catalyst above a temperature to combust gas analytes of interest, and electronic circuitry in operative connection with the heating element of the first sensing element to periodically cycle the first sensing element between a temperature above the temperature to combust the analytes of interest and a temperature at which the catalyst is substantially inactive to catalyze oxidative combustion of the analytes of interest. The electronic circuitry is adapted to determine a species of at least one of the gas analytes of interest from a first output of the combustible gas sensor during an ON time within a cycle duration. The electronic circuitry is further adapted to determine a concentration of the species of gas from a second output of the combustible gas sensor. The catalyst may, for example, be heated above a temperature to combust methane during the ON time. The combustible gas sensor may further include a first compensating element in operative connection with the electronic circuitry.

In a number of embodiments, the first sensing element has a thermal constant of 8 second or less or 6 seconds or less. The first sensing element may, for example, comprise a MEMS pellistor or or a pelement of low thermal mass to provide a thermal constant of 8 seconds or less (or 6 seconds or less).

In a number of embodiments, the ON time during the cycle duration is between 100 msec and 1 sec. In a number of embodiments, the ON time during the cycle duration is between 300 msec and 500 sec. The duty cycle of the periodic cycling of the first sensing element may, for example, be in the range of 5 to 12%. In a number of embodiments, the duty cycle of the periodic cycling of the first sensing element is in the range of 8 to 11%.

The dynamic output of an individual cycle may be analyzed to determine the first output and the species of at least one of the gas analytes of interest after the combustible gas sensor hereof has reached a stable output or prior to the combustible gas sensor reaching a stable output.

The combustible gas sensor may further include a housing including an inlet. The first sensing element may be positioned within the housing. The combustible gas sensor may further include at least one filter, the at least one filter being adapted to remove (either partially or completely) at least one substance other than the analytes of interest.

The concentration may, for example, be a predetermined threshold concentration (for example, a threshold concentration related to a lower explosive limit or LEL) and the electronic circuitry is further adapted to generate an alarm signal. The determination of the threshold concentration may, for example, occur before the output signal or response of the combustible gas sensor reaches a stable output. The combustible gas sensor may further determine the concentration of the species of at least one of the gas analytes of interest in the surrounding environment upon reaching a stable output or before the output signal/response reaches a stable output.

In another aspect, a method of operating a combustible gas sensor (wherein the combustible gas sensor has a first sensing element, the first sensing element including a catalyst and a heating element in operative connection with the catalyst to heat the catalyst above a temperature to combust gas analytes of interest, and electronic circuitry in operative connection with the heating element of the first sensing element) includes periodically cycling the first sensing element via the electronic circuitry between the temperature above the temperature to combust the analytes of interest and a temperature at which the catalyst is substantially inactive to catalyze oxidative combustion of the analytes of interest. The electronic circuitry determines a species of at least one of the gas analytes of interest from a first output of the combustible gas sensor during an ON time within a cycle duration and determines a concentration of the species of gas from a second output of the combustible gas sensor. The combustible gas sensor may further include a first compensating element in operative connection with the electronic circuitry. In a number of embodiments, the catalyst is heated above a temperature to combust methane during the ON time.

The first sensing element may, for example, have a thermal constant of 8 second or less (or 6 seconds or less). As described above, the first sensing element may, for example, be formed as a MEMS pellistor or a lower-thermal-mass pellistor. In a number of embodiments, the ON time during the cycle duration is between 100 msec and 1 sec or between 300 msec and 500 sec. The duty cycle of the periodic cycling of the first sensing element may, for example, be in the range of 5 to 12% or 8 to 11%.

As described above, the dynamic output of an individual cycle is analyzed to determine the first output and the species of at least one of the gas analytes of interest. The determination of the species may, for example, be made after the combustible gas sensor hereof has reached a stable output of before the combustible gas sensor has reached a stable output. A species of more than one of the gas analytes of interest may, for example, be determined from the dynamic output of the combustible gas sensor during an ON time within the cycle duration.

In a number of embodiments, the combustible gas sensor further includes a housing having an inlet, and the first sensing element is positioned within the housing. The method may, for example, further include providing at least one filter, wherein the at least one filter removes (either partially or completely) at least one substance other than the analytes of interest.

As described above, the concentration determined may, for example, be a predetermined threshold concentration and the electronic circuitry may further generate an alarm signal.

In a further aspect, a method of identifying a species of at least one of a plurality gas analytes of interest includes periodically cycling a first sensing element including a catalyst and having a thermal time constant less than 8 seconds between a temperature above a temperature to combust the plurality of analytes of interest and a temperature at which the catalyst is substantially inactive to catalyze oxidative combustion of the analytes of interest and determining a species of at least one of the gas analytes of interest from an output of the combustible gas sensor during an ON time within a cycle duration. In a number of embodiments, the thermal time constant is less than 6 seconds.

In still a further aspect, a system includes a first combustible gas sensor including a first housing having a first inlet, a first filter in operative connection with the first inlet of the housing, and a first sensing element within the housing. The first sensing element includes a first catalyst and a first heating element in operative connection with the first catalyst to heat the first catalyst above a temperature to combust gas analytes of interest for the first combustible gas sensor. The first combustible gas sensor further includes first electronic circuitry in operative connection with the first heating element of the first sensing element to periodically cycle the first sensing element between a temperature above the temperature to combust the analytes of interest for the first combustible gas sensor and a temperature at which the first catalyst is substantially inactive to catalyze oxidative combustion of the analytes of interest for the first combustible gas sensor. The first filter is adapted to remove at least one substance other than the analytes of interest for the first combustible gas sensor. The first electronic circuitry is adapted to determine a species of at least one of the gas analytes of interest for the first combustible gas sensor from a first output of the first combustible gas sensor during an ON time within a cycle duration of the first combustible gas sensor. The first electronic circuitry is further adapted to determine a concentration of the species of gas from a second output of the first combustible gas sensor.

The system further includes a second combustible gas sensor including a second housing having a second inlet, a second filter, different from the first filter, in operative connection with the second inlet, and a second sensing element within the housing. The second sensing element includes a second catalyst and a second heating element in operative connection with the second catalyst to heat the second catalyst above a temperature to combust gas analytes of interest for the second combustible gas sensor. The second combustible gas sensor further includes second electronic circuitry in operative connection with the second heating element of the second sensing element to periodically cycle the second sensing element between a temperature above the temperature to combust the analytes of interest for the second combustible gas sensor and a temperature at which the second catalyst is substantially inactive to catalyze oxidative combustion of the analytes of interest for the second combustible gas sensor. The second filter is adapted to remove at least one substance other than the analytes of interest for the second combustible gas sensor. The second electronic circuitry is adapted to determine a species of at least one of the gas analytes of interest for the second combustible gas sensor from transient first output of the second combustible gas sensor during an ON time within a cycle duration of the second combustible gas sensor. The second electronic circuitry is further adapted to determine a concentration of the species of gas from a second output of the second combustible gas sensor.

The present devices, systems, and methods, along with the attributes and attendant advantages thereof, will best be appreciated and understood in view of the following detailed description taken in conjunction with the accompanying drawings.

DETAILED DESCRIPTION

Figure 1A:
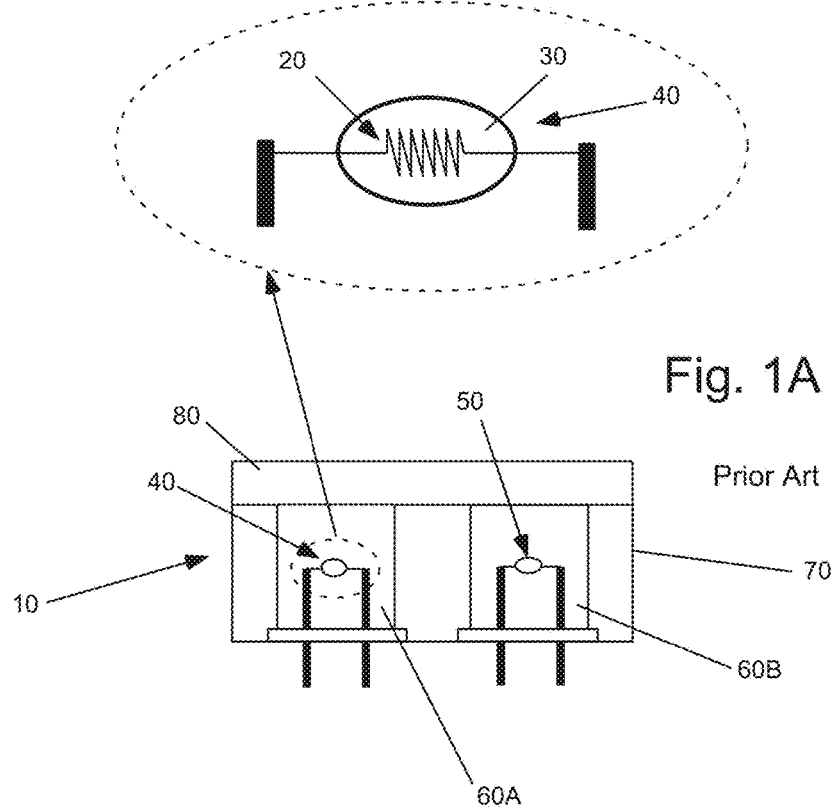
FIG. 1A illustrates an embodiment of a conventional combustible gas sensor.

It will be readily understood that the components of the embodiments, as generally described and illustrated in the figures herein, may be arranged and designed in a wide variety of different configurations in addition to the described representative embodiments. Thus, the following more detailed description of the representative embodiments, as illustrated in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "an element" includes a plurality of such elements and equivalents thereof known to those skilled in the art, and so forth, and reference to "the element" is a reference to one or more such elements and equivalents thereof known to those skilled in the art, and so forth.

Recitation of ranges of values herein are merely intended to serve as a shorthand method of referring individually to each separate value falling within the range. Unless otherwise indicated herein, and each separate value, as well as intermediate ranges, are incorporated into the specification as if individually recited herein. All methods described herein can be performed in any suitable order unless otherwise indicated herein or otherwise clearly contraindicated by the text.

The terms "electronic circuitry", "circuitry" or "circuit," as used herein includes, but is not limited to, hardware, firmware, software or combinations of each to perform a function(s) or an action(s). For example, based on a desired feature or need. a circuit may include a software controlled microprocessor, discrete logic such as an application specific integrated circuit (ASIC), or other programmed logic device. A circuit may also be fully embodied as software. As used herein, "circuit" is considered synonymous with "logic." The term "logic", as used herein includes, but is not limited to, hardware, firmware, software or combinations of each to perform a function(s) or an action(s), or to cause a function or action from another component. For example, based on a desired application or need, logic may include a software controlled microprocessor, discrete logic such as an application specific integrated circuit (ASIC), or other programmed logic device. Logic may also be fully embodied as software.

The term "processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

The term "software," as used herein includes, but is not limited to, one or more computer readable or executable instructions that cause a computer or other electronic device to perform functions, actions, or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, or the desires of a designer/programmer or the like.

In several embodiments, pulse width modulation was used to control the energy delivered to the hotplates. Pulse width modulation is a well-known control technique used to control the average power and/or energy delivered to a load. In embodiments hereof, a voltage is supplied to, for example, a MEMS hotplate or other heating element to heat the supported catalyst to a desired temperature. Because the pellisters or pelements hereof have relatively low thermal mass, the cycle times can be relatively short.

Heating energy (that is, heating voltage(s) or heating currents(s)) may be periodically supplied to the heating element(s) during an "ON time". Rest energy (that is, rest voltage(s) or a rest current(s)), which is less than the heating energy may be supplied during a "REST time". The total of the higher-energy or ON time plus the lower-energy or REST time correspond to a cycle time or a cycle duration. Gas concentration or the analyte is measured during the ON time. The heating energy (voltages/currents) supplied during the ON time may be constant during the ON time or may be varied (for example, supplied as heating voltage/current plateau or as heating voltage/current ramp). The rest energy (voltages/currents) may be equal to zero, or be sufficiently lower than the heating energy so that the gas sensor does not consume any gas or substantially any gas to be detected. Similar to the ON time, the rest energy supplied during the REST time may be constant during all the REST time or may be varied (for example, supplied as rest voltage/current plateau or as rest voltage/current ramp). The cycle may be repeated.

Figure 1B:
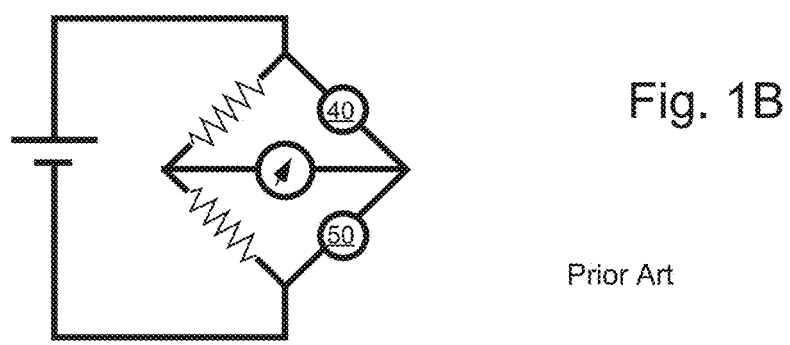
FIG. 1B illustrates an enlarged view of a Wheatstone bridge circuit incorporating the sensing element and the compensating element of the combustible gas sensor of FIG. 1A.

Conventional catalytic combustible gas detectors are operated in a Wheatstone bridge as, for example, described in connection with FIG. 1B, in constant current or constant voltage. As described above, such sensors are powered to run the pelements or hotplates in, for example, a temperature range of 350-600° C. whenever the sensor is operational. This mode of operation may be termed a "continuous" mode of operation. An alternate operational mode, which is particularly suitable for-low mass pelements or MEMS hotplates/pellistors, is to quickly heat and cool the detector in a pulsed power mode. Low mass pelements are, for example, described in U.S. Pat. No. 8,826,721, the disclosure of which is incorporated herein by reference. An advantage to operating in pulse mode is significantly lower power consumption as compared to continuous mode. Another advantage is improved span response as a result of adsorption of excess combustible gas on the catalyst at cooler temperatures during unpowered or lower powered operation (that is, during the REST time) as compared to continuously powering the catalyst at the run temperature of 350-600° C.

As used herein, the term "MEMS pellistor" refers to a sensor component with dimensions less than 1 mm that is manufactured via microfabrication techniques. In a number of representative embodiments, sensing elements formed as MEMS pellistors hereof may be manufactured with a thick film catalyst, powered to an operating temperature by resistive heating and are used to detect combustible gases. In a number of representative embodiments, the thickness and diameter for a MEMS catalyst film is 15 microns and 650 microns, respectively.

Figure 2:
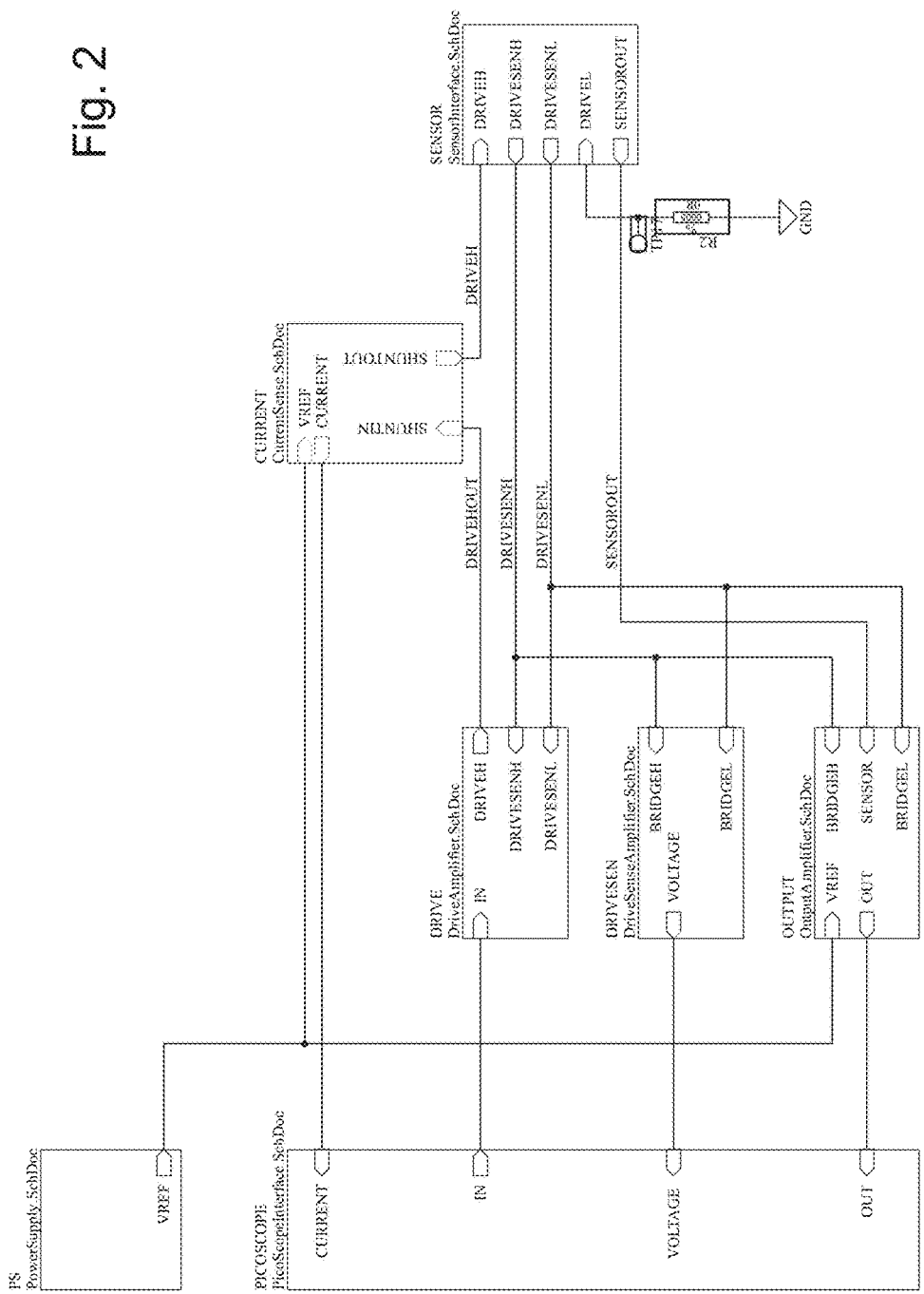
FIG. 2 illustrates a schematic representation of sensor interface electronics for an embodiment of a detector hereof.

A representative embodiment of electronic circuitry for an embodiment of a MEMS pellistor 100 (see FIGS. 3A and 3B) used in a number of studies hereof is illustrated schematically in FIG. 2. The output of MEMS pellistor 100 may, for example, be measured by connecting it as two arms of a Wheatstone bridge as described in connection with FIG. 1B. This method of measuring output is a straightforward and reliable method of comparing the relative change of a resistance. In a number of studies, a representative 6V DC power supply was used, which was regulated to a stable 5V via a linear voltage regulator. A 1.25V voltage reference was used to bias the output amplifier. The drive waveform in the studied embodiments was provided by the PicoScope oscilloscope available from Pico Technology of Tyler, Tex. The Wheatstone bridge was driven by an OPA567 high current, high speed amplifier available from Texas Instruments of Dallas, Tex. A drive voltage sense circuit monitored the voltage across the sensor using the bridge sense wires. The drive voltage sense circuit provides a check that the drive amplifier is functioning and the sensor is connected correctly. In the studied embodiment, a current sense amplifier used fixed gain high side current sense integrated circuit or IC, which has a very low offset voltage to allow the use of small shunt resistors. By including the current sense shunt in the cable compensation feedback loop, the shunt resistance does not affect the voltage at the sensor. The shunt resistor and amplifier gain were chosen to give a gain of 25 V/A (that is, 1V output at the nominal sensor current of 40 mA). An output amplifier converts the differential bridge output signal to a single ended voltage for the oscilloscope. It also provides some amplification to reduce the impact of noise. A sensor interface on a printed circuit board (PCB) was formed from 2×2-pin LEMO push/pull connectors (available from LEMO USA, Inc. of Rohnert Park, Calif.) for the bridge drive and sense and a single BNC connector for the MEMS pellistor output node. The part of the electronics that holds the sensor was split into two parts. A larger holder PCB (not shown) hosted the LEMO and BNC connectors, with the sensor 100 mounted on small, inexpensive sensor breakout PCB 200.

Figure 3A:
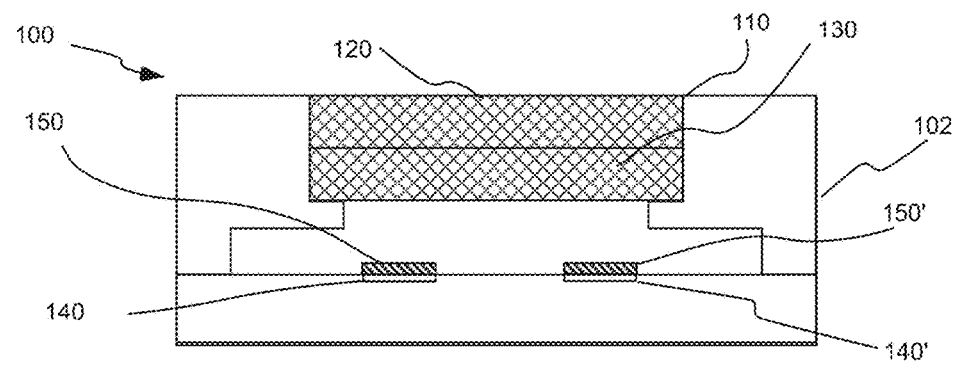
FIG. 3A illustrates an embodiment of a MEMS pellistor hereof.

FIG. 3A illustrates a cutaway view of an embodiment of a MEMS pellistor, which includes a housing 102 having a gas inlet 110. A screen or cap 120, which may include or function as a filter 130, may, for example, be placed in connection with inlet 110. The energy (current and voltage) used in pellistor 100 may, for example, be sufficiently low to provide intrinsic safety such that a flashback arrestor, as known in the combustible gas detector arts, may not be necessary. Flashback arrestors (for example, porous frits) allow ambient gases to pass into a housing but prevent ignition of combustible/flammable gas in the surrounding environment by hot elements within the housing. One or more heating elements or hotplates 140 may be used to heat an oxidative catalyst layer 150 to operating temperature. A MEMS compensating element or compensator may be included within MEMS pellistor 100. As described above, MEMS compensator may include an inactive layer 150' which may be heated by one or more heating elements or hotplates 140'. Alternatively layer 150' may include an active catalyst and be operated at a sufficiently low temperature to prevent oxidation of combustible gas. MEMS pellistor 100 is mounted on a PCB 200 as described above. In a number of studies, a SGX MP7217 pellistor available from SGX Sensortech, SA of Corcelles-Coromondreche, Switzerland was used in the studied systems hereof.

Figure 4A:
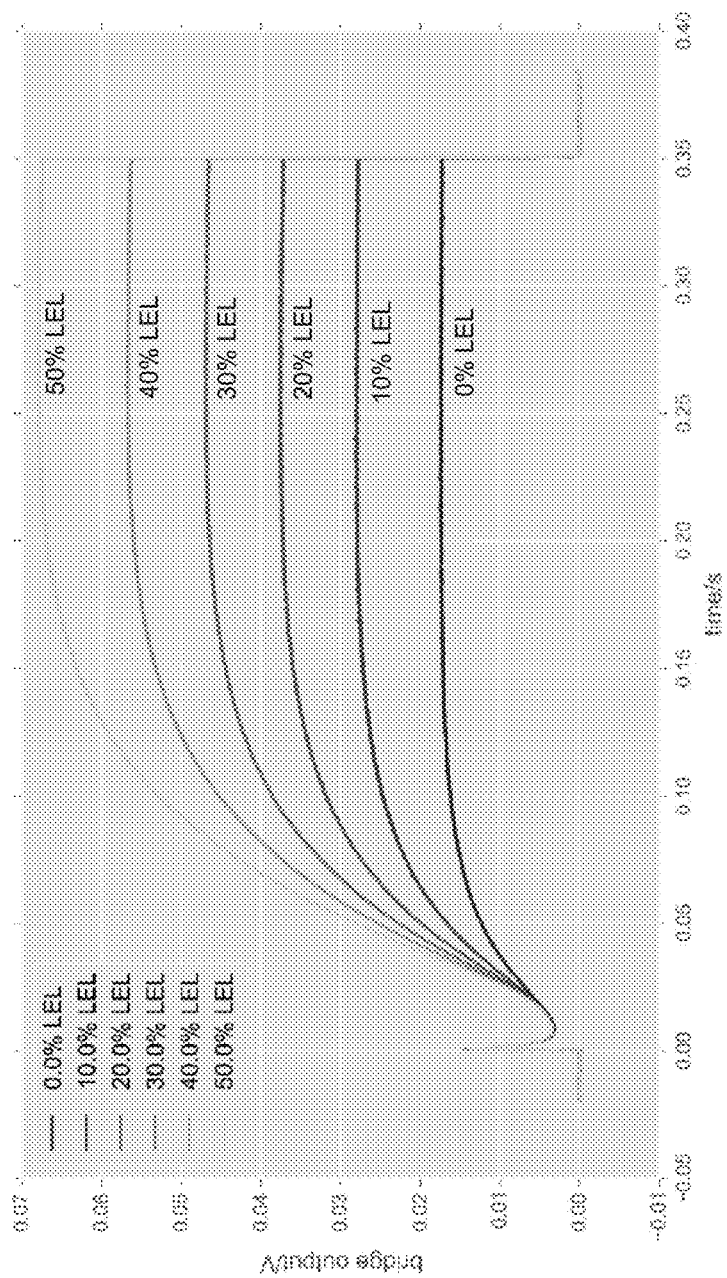
FIG. 4A illustrates a response of a detector hereof to various levels of methane gas over a pulse of 350 msec.
Figure 4B:
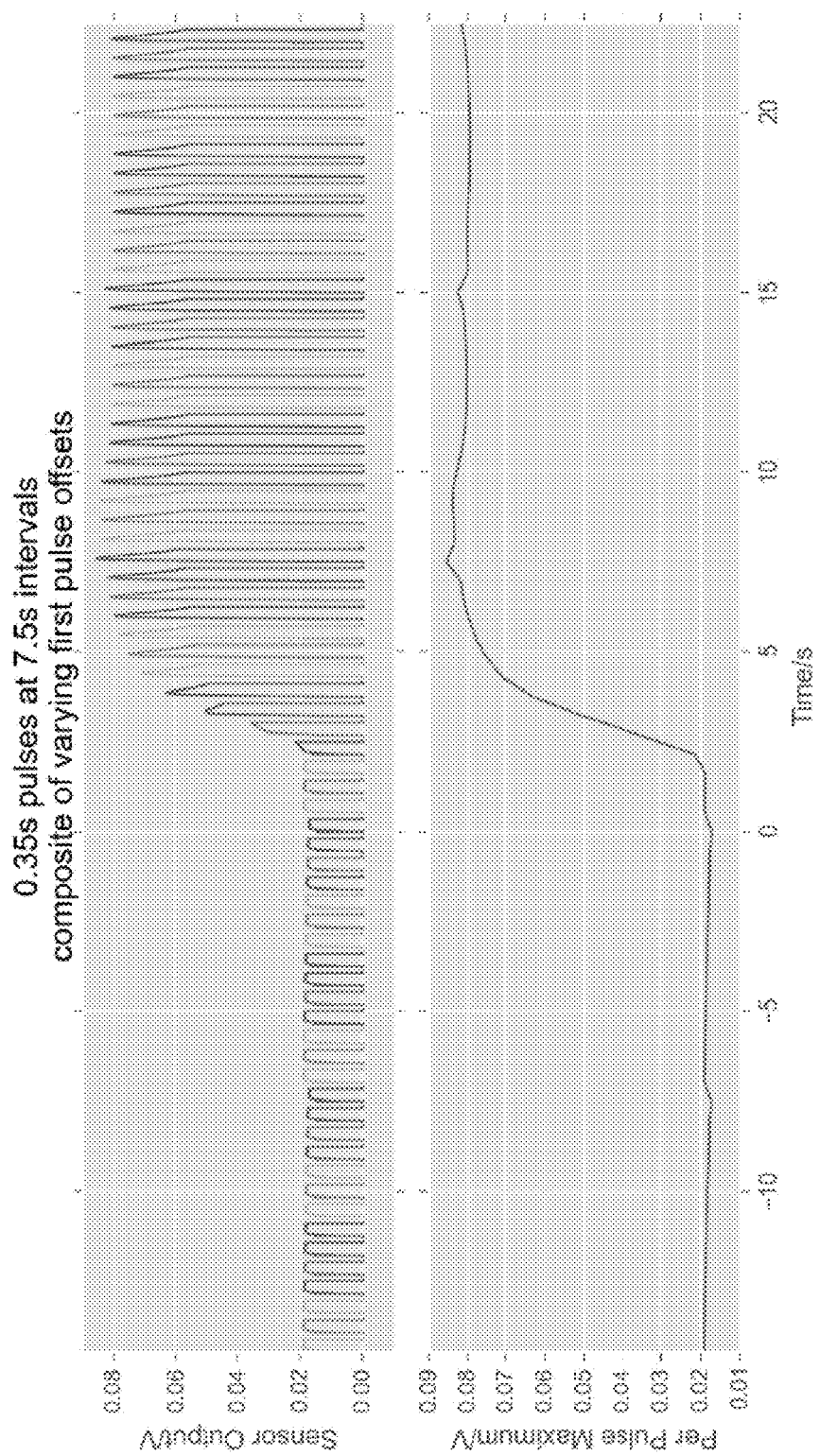
FIG. 4B illustrates detector output before and after the introduction of hydrogen gas for 350 msec pulses at 7.5 s intervals wherein the data set forth is a composite of studies with varying first pulse offsets.
Figure 4C:
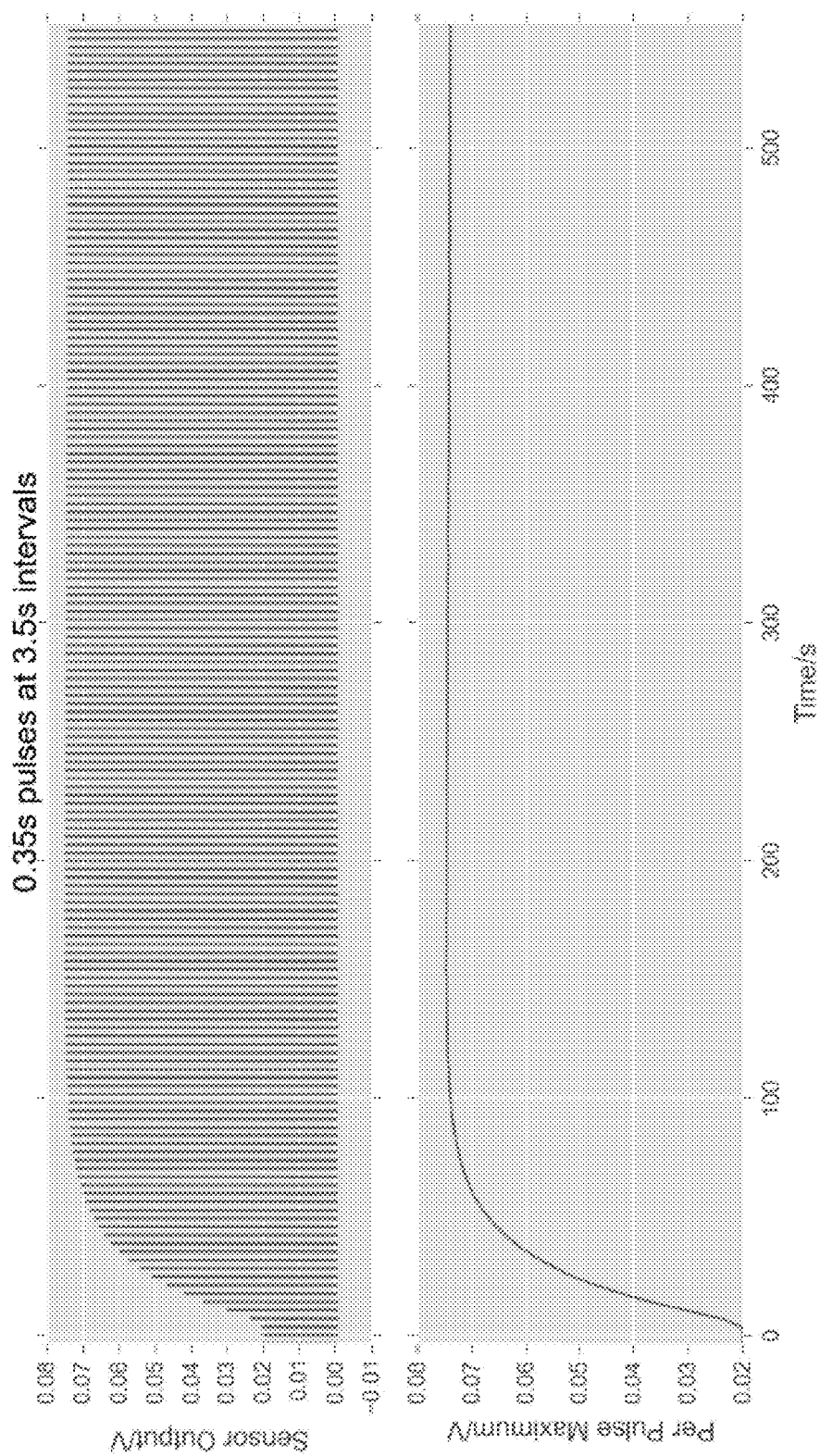
FIG. 4C illustrates detector output before and after the introduction of pentane gas for 350 msec pulses at 3.5 s intervals.

FIG. 4A illustrates a response of a detector hereof to various levels of methane over a powered pulse or ON time of 350 msec. FIGS. 4B and 4C illustrate studies to determine a $t_{90}$ of a detector hereof (that is, the time to reach 90% of the full response) for hydrogen gas and propane gas, respectively. To calculate $t_{90}$ in the studies of FIGS. 4B and 4C, a per pulse algorithm was used. The maximum value for each on-time pulse was determined. The minimum and maximum values of those points were determined, and the minimum was subtracted from the maximum. The per-pulse maxima curve was interpolated to find the times when: (a) the reading rose above the minimum of +2% of the span, and (b) the reading rose above the minimum +90% of the span. These two times were used provide the $t_{90}$ value. FIG. 4B illustrates the response of a detector hereof to the introduction of hydrogen gas wherein the power to the heating element was cycled with a 350 msec (0.35 sec) ON time and a cycle duration of 7.5 second. In FIG. 4B, composite data from runs with varying first ON time offsets are set forth. A $t_{90}$ of 4.1 second was determined for the non-optimized experimental sensor studied. FIG. 4C illustrates the response of a non-optimized experimental sensor hereof to the introduction of propane gas wherein the power to the heating element was cycled with a 350 msec ON time and a 3.5 second cycle duration. A $t_{90}$ of 56.1 seconds was determined for the experimental sensor studied.

Figure 5:
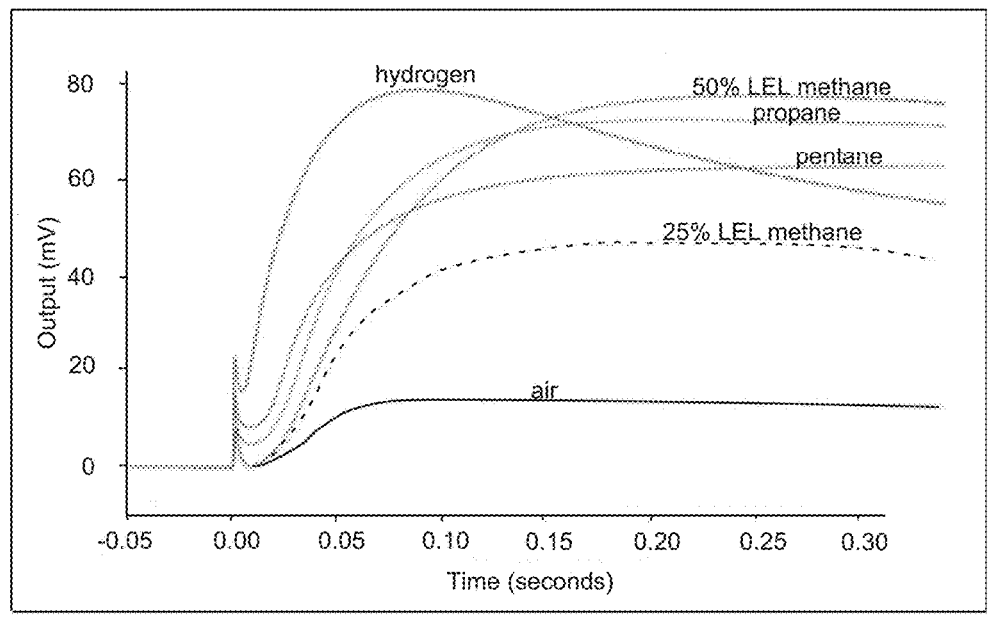
FIG. 5 illustrates sensor output curves for methane, hydrogen gas, propane gas and pentane gas.

In a number of studies hereof, after the pulse mode operated catalytic combustible gas detector hereof reached a stable output for a constant concentration of combustible gas, examination of the individual pulse response yielded additional information about the chemical composition of the gas as a result of adsorption on the unpowered or lower powered catalyst (that is, during the REST time) observed in combination with the heating ramp of the catalyst when power is cycled on. The concentration of analyte gas within the sensor and in contact with the sensing element eventually reaches concentration equilibrium with the environment. Before equilibrium is reached, the concentration detected by the sensor is increasing. After equilibrium is reached, the output may be considered "stable". Equilibrium or stability in output may, for example, be considered to be reached when the output changes by less than a predetermined amount of a predetermined period of time. For example, stability may be defined as three successive readings, taken 2 minutes apart, indicate no change greater than ±1% of the measuring range. FIG. 5 shows the Wheatstone bridge output from catalytic MEMS pellistor 100 with matched detecting and compensating elements (as described above) with power pulsed on at time=0 and the resultant response to hydrogen, propane, pentane, and methane at concentrations of 50% lower explosion level (LEL). FIG. 5 also shows output for methane at 25% LEL. The initial peak at 4 msec is attributed to an electronic heating effect of the two matched hotplates 140 and 140'. However, its magnitude appears to vary by chemical. FIG. 5 illustrates that when the sensor is exposed to 50% LEL methane, the increasing concentration curves provides the same "light off" information as the 25% LEL curve. As illustrated in FIG. 5 each response curve would result in identification or speciation as methane. FIG. 5 demonstrates that there is no need to wait for concentration stability with the environment to achieve identification or speciation.

Figure 6:
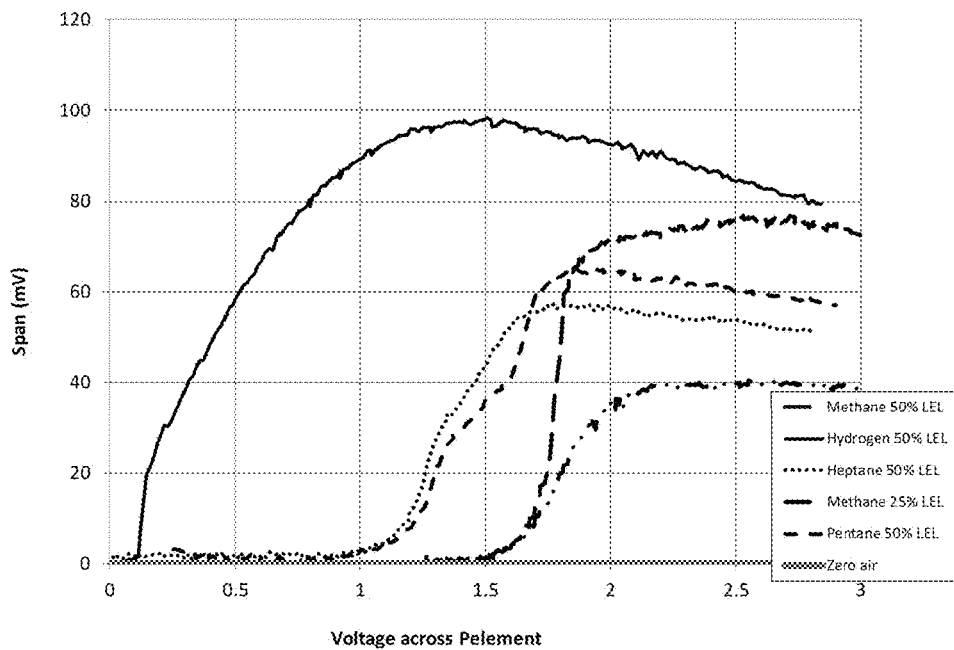
FIG. 6 illustrates catalytic oxidation light-off curves for methane gas, hydrogen gas, heptane gas, and pentane gas.

Following the initial peak, examination of the 350 msec ON time shows qualitatively similar behavior to classical catalyst light-off curves obtained by temperature ramping a catalyst in the presence of combustible gases as illustrated in FIG. 6. Among common hydrocarbons, methane requires the highest temperature for combustion, hydrogen requires low temperatures, and larger alkanes fall in between, with longer to shorter carbon chain requiring lower to higher light-off temperatures. In FIG. 5, this light-off order may, for example, be obtained from pulse data by, for example, measuring time required to reach a defined output (for example, a 30 mV output) which corresponds to the order $H_2 < C_5 < C_3 < C_1$. This order is the same order observed on the catalyst in FIG. 6 for voltages required to produce 30 mV which correspond to the order $H_2 < C_7 < C_5 < C_1$. For the pulse mode of operation, the light-off information also correlates with the order of the span exhibited by the initial power-on peak at 4 msec in FIG. 5, with $C_1 < C_3 < C_5 < H_2$.

There are additional similarities between the pulse data and catalyst light-off data in the concentration regime. Specifically, initial methane responses at 25% and 50% LEL exhibit similar pulse shapes at short times independent of concentration. Without limitation to any mechanism, the most active sites for methane will oxidize the adsorbed gases at the same temperature at the beginning of the light-off curve. This is the same behavior observed at low light-off voltages for 25% and 50% LEL methane.

It is well known that conventional combustible sensors operated in continuous mode reach a steady state value dependent on the concentration and chemical character of the target combustible gas. Detector manufacturers determine the expected ratio of span response of the target gas to a calibration gas, both experimentally and theoretically, and publish tables of "response factors" to aid in quantification of a known target gas. Referring to FIG. 5, values after the ON time pulse has been on more than 150 msec correlate reasonably well with response factors in similar chemistry oxidation catalyst systems as shown in FIG. 6 past methane light-off temperatures. Therefore, the pulsed mode provides all the information currently obtained from continuously operated catalytic combustible sensors, in addition to new light-off information.

Studies of the detectors hereof indicated that the ON time duration may, for example, be in the range of 100 msec to 1 second or in the range of 300 msec to 500 msec in a number of embodiments hereof. In a number of embodiments, the ON time duration is kept as short as possible to improve response time. In a number of embodiments, the duty cycle may, for example, be in the range of 5% to 12%. In a number of embodiments, the ON time is approximately 350 msec (that is, equal to or within 10% of that) and the duty cycle is approximately 10% (that is, equal to or within 20% of that value). In a representative example, the cycle time or cycle duration was 4000 ms, during which the ON time was 350 ms and the REST time was 3650 ms. Therefore, the duty cycle is 8.75%.

It is very difficult and slow to obtain light-off type data using currently available sensors operated at constant voltage or constant current with a Wheatstone bridge. One problem with running catalysts for long periods of time at low temperatures is formation of incomplete combustion products such as solid carbon, known as coke, which can deactivate the catalyst for oxidation reactions and reduce span. Moreover, many conventional pelements require on the order of tens of seconds to heat up to light-off temperatures, which is impractically long for response times required by agencies and combustible sensor users.

To the contrary, determining or identifying the species of combustible gases using the fast pulse technique hereof to obtain information related to the chemical composition is quickly achieved. The methodology hereof is particularly useful for low mass catalytic sensors formed on a MEMS hotplate heater or on a fine wire helical heater. As described above, conventional continuous mode operation can provide quantitative information about a known target gas using a manufacturer published response factor. However identification of the target gas is not possible with conventional catalytic combustible sensors and must be accomplished using separate industrial hygiene methods involving more specific, sophisticated, expensive and possibly off-line detectors such as gas chromatography, infrared spectroscopy, mass spectroscopy, and the like. A catalytic combustible detector with chemical speciation capabilities greatly improves the state of the art in combustible gas detector safety technology.

Figure 3B:
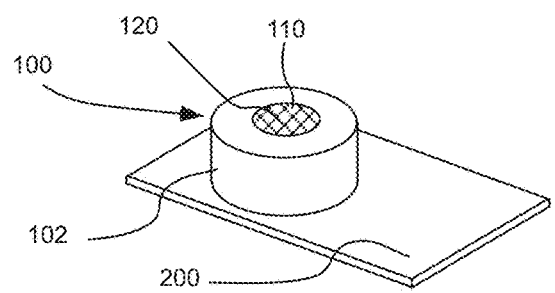
FIG. 3B illustrates a MEMS sensing pellistor and a MEMS compensator pellistor hereof mounted on printed circuit boards.
Figure 3C:
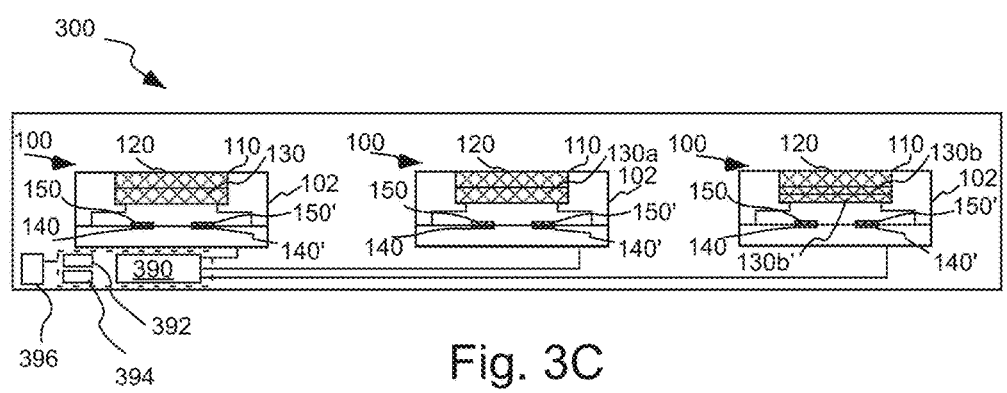
FIG. 3C illustrates a system comprising a plurality of combustible gas sensors such as illustrated in FIGS. 3A and/or 3B wherein each of the combustible gas sensors includes a different filter.

Furthermore, an array of pulsed sensors in a system 300 (see FIG. 3C) may be positioned behind different filter materials to allow further chemical speciation and concentration determination. The low power requirements possible for the detectors hereof make use of an array of sensors more feasible than using presently available continuous mode technology. For example, activated carbon can allow passage of light hydrocarbon analytes, including methane, hydrogen, and methanol, to the catalyst while blocking longer chain hydrocarbons. Another example is a filter made of a hydrophilic adsorbent such as silica gel, which would allow passage of alkanes while blocking polar species such as alcohols or amines. There are numerous examples of preferential filtration by chemical species in the literature for adsorbent gas chromatograph columns. As applied upstream of combustible pellistors, these filters could be used separately or in combination to allow passage of analytes with specific chemical characteristics. FIG. 3C illustrates schematically a system including, for example, three sensors 100 as described above in connection with FIGS. 3A and 3B. Each of sensors 100 of system 300 may, for example, include at least one filter 130, 130a, 130b and 130b', wherein rightmost sensor 100 in FIG. 3B is illustrated to include two filters 130b and 130b'. Each of filters 130, 130a, 130b and 130b' may, for example, filter different substances which pass through inlet 110. Electronic circuitry 390 may, for example, be in operating connection with each of sensors 100 to, for example, control power to sensors 100' (as described above) and to process an output signal from sensors 100. Electronic circuitry 390 may, for example, include or be in operative connection with a processor system 392 (including, for example, one or more processors such as microprocessors) and a memory system 394. One or more algorithms for control of sensors 100 and/or for processing of data may, for example, be stored in memory system 394, which is in operative connection with processor system 392. Output of sensors 100 may, for example, be provided to a user or users via a user interface 396 (for example, including a display) in operative connection with processor system 392. A user interface 396 may, for example, be provided as a component of the combustible gas sensor and/or remote from the combustible gas sensor. An alarm signal may, for example, be generated via electronic circuitry 390 and provided to a user via one or more components of user interface 396 (for example, visually, audibly etc.). Electronic circuitry 390, as described in connection with system 300, may for example, be used in connection with a single combustible gas sensor such as sensor 100 of FIGS. 3A and 3B.

Figure 7:
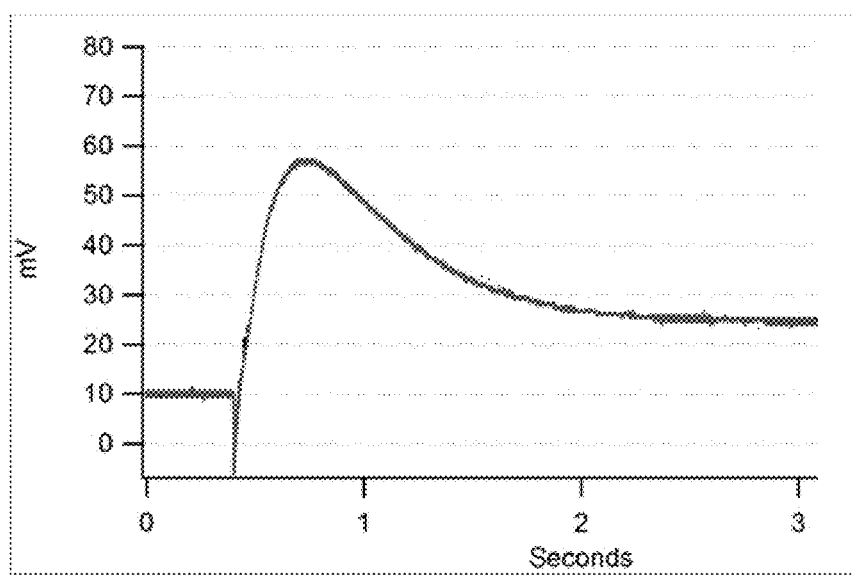
FIG. 7 illustrates sensor output for a low-mass pelement.

In a number of embodiments, sensing elements for use herein have thermal time constant of 8 seconds or less or 6 second or less. The thermal time constant of a sensing element is defined as the time required to change 63.2% of the total difference between its initial and final temperature when subjected to a step function change in drive power, under zero power initial conditions. Although the representative data illustrated in FIG. 5 were obtained using a catalytic MEMS pellistor, similar data may be obtained using a pelement pair having a sufficiently low mass. For example FIG. 7 shows pulse data obtained when a 450 micron diameter pelement having a catalyst mass of approximately 75 micrograms was heated in air for an ON time of 3 seconds. The initial power-on peak is opposite in sign as compared to the MEMS pellistor response illustrated in FIG. 5. The initial power-on peak also changes direction for selected MEMS hotplate samples, depending on the resistance matching of the detecting and compensating elements of the MEMS pellistor. Sensors including low thermal mass suitable for use herein are, for example, disclosed in U.S. Pat. No. 8,826,721 may be used herein.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A combustible gas sensor, comprising a first sensing element, the first sensing element comprising a catalyst and a heating element in operative connection with the catalyst to heat the catalyst above a temperature to combust a plurality of different gas analytes of interest, and electronic circuitry in operative connection with the heating element of the first sensing element and configured to periodically cycle the first sensing element between a temperature above the temperature to combust the plurality of different gas analytes of interest and a temperature at which the catalyst is substantially inactive to catalyze oxidative combustion of the plurality of different gas analytes of interest, the electronic circuitry being configured to determine a species of at least one of the plurality of different gas analytes of interest from a first output of the combustible gas sensor during an ON time within a cycle duration as the temperature of the first sensing element is increasing and the electronic circuitry is further configured to determine a concentration of the species of the at least one of the plurality of different gas analytes of interest from a second output of the combustible gas sensor.

2. The combustible gas sensor of claim 1 wherein the first sensing element is a sensing element of a MEMS pellistor.

3. The combustible gas sensor of claim 1 wherein the first sensing element has a thermal constant of 8 second or less.

4. The combustible gas sensor of claim 2 wherein the ON time during the cycle duration is between 100 msec and 1 sec.

5. The combustible gas sensor of claim 2 wherein the ON time during the cycle duration is between 300 msec and 500 msec.

6. The combustible gas sensor of claim 1 wherein a duty cycle of the periodic cycling of the first sensing element is in the range of 5 to 12%.

7. The combustible gas sensor of claim 1 wherein a duty cycle of the periodic cycling of the first sensing element is in the range of 8 to 11%.

8. The combustible gas sensor of claim 1 further comprising a first compensating element in operative connection with the electronic circuitry.

9. The combustible gas sensor of claim 1 wherein the catalyst is heated above a temperature to combust methane.

10. The combustible gas sensor of claim 1 further comprising a housing comprising an inlet, the first sensing element being positioned within the housing, and at least one filter, the at least one filter being adapted to remove at least one substance other than the plurality of gas analytes of interest.

11. The combustible gas sensor of claim 1 wherein the concentration is a predetermined threshold concentration and the electronic circuitry is further adapted to generate an alarm signal.

12. A method of operating a combustible gas sensor having a first sensing element, the first sensing element comprising a catalyst and a heating element in operative connection with the catalyst to heat the catalyst above a temperature to combust a plurality of different gas analytes of interest, and electronic circuitry in operative connection with the heating element of the first sensing element, comprising: periodically cycling the first sensing element via the electronic circuitry between the temperature above the temperature to combust the plurality of different gas analytes of interest and a temperature at which the catalyst is substantially inactive to catalyze oxidative combustion of the plurality of different gas analytes of interest, the electronic circuitry determining a species of at least one of the plurality of different gas analytes of interest from a first output of the combustible gas sensor during an ON time within a cycle duration as temperature of the first sensing element is increasing and determining a concentration of the species of the at least one of the plurality of different gas analytes of interest from a second output of the combustible gas sensor.

13. The method of claim 12 wherein the first sensing element is formed as a MEMS pellistor.

14. The method of claim 12 wherein the first sensing element has a thermal constant of 8 second or less.

15. The method of claim 13 wherein the ON time during the cycle duration is between 100 msec and 1 sec.

16. The method of claim 13 wherein the ON time during the cycle duration is between 300 msec and 500 msec.

17. The method of claim 12 wherein a duty cycle of the periodic cycling of the first sensing element is in the range of 5 to 12%.

18. The method of claim 12 wherein a duty cycle of the periodic cycling of the first sensing element is in the range of 8 to 11%.

19. The method of claim 12 wherein the combustible gas sensor further comprises a first compensating element in operative connection with the electronic circuitry.

20. The method of claim 12 where a species of more than one of the gas analytes of interest is determined from a transient output of the combustible gas sensor during an ON time within the cycle duration.

21. The method of claim 12 wherein the catalyst is heated above a temperature to combust methane.

22. The method of claim 12 wherein the combustible gas sensor further comprises a housing comprising an inlet, the first sensing element being positioned within the housing, the method further comprising providing at least one filter, the at least one filter removing at least one substance other than the plurality of different gas analytes of interest.

23. The method of claim 12 wherein the concentration is a predetermined threshold concentration and the method further comprising generating an alarm signal via the electronic circuitry upon determining the predetermined threshold concentration.

24. A method of identifying a species of at least one of a plurality of different gas analytes of interest; comprising periodically cycling a first sensing element including a catalyst and having a thermal time constant less than 8 seconds between a temperature above a temperature to combust the plurality of different gas analytes of interest and a temperature at which the catalyst is substantially inactive to catalyze oxidative combustion of the plurality of different gas analytes of interest and determining a species of at least one of the plurality of different gas analytes of interest from a dynamic output of the combustible gas sensor during an ON time within a cycle duration.

25. A system comprising: a first combustible gas sensor comprising a first housing having a first inlet, a first filter in operative connection with the first inlet of the housing, a first sensing element within the housing, the first sensing element comprising a first catalyst and a first heating element in operative connection with the first catalyst to heat the first catalyst above a temperature to combust a plurality of different gas analytes of interest for the first combustible gas sensor, and first electronic circuitry in operative connection with the first heating element of the first sensing element and configured to periodically cycle the first sensing element between a temperature above the temperature to combust the plurality of different gas analytes of interest for the first combustible gas sensor and a temperature at which the first catalyst is substantially inactive to catalyze oxidative combustion of the plurality of different gas analytes of interest for the first combustible gas sensor, the first filter being configured to remove at least one substance other than the plurality of different gas analytes of interest for the first combustible gas sensor, the first electronic circuitry being configured to determine a species of at least one of the plurality of different gas analytes of interest for the first combustible gas sensor from a first output of the first combustible gas sensor during an ON time within a cycle duration of the first combustible gas sensor as temperature of the first sensing element is increasing and the first electronic circuitry is further configured to determine a concentration of the species of at least one of the plurality of different gas analytes of interest for the first combustible gas sensor from a second output of the first combustible gas sensor, and a second combustible gas sensor comprising a second housing having a second inlet, a second filter, different from the first filter, in operative connection with the second inlet, a second sensing element within the housing, the second sensing element comprising a second catalyst and a second heating element in operative connection with the second catalyst to heat the second catalyst above a temperature to combust a plurality of different gas analytes of interest for the second combustible gas sensor, and second electronic circuitry in operative connection with the second heating element of the second sensing element to and configured periodically cycle the second sensing element between a temperature above the temperature to combust the plurality of different gas analytes of interest for the second combustible gas sensor and a temperature at which the second catalyst is substantially inactive to catalyze oxidative combustion of the plurality of different gas analytes of interest for the second combustible gas sensor, the second filter being configured to remove at least one substance other than the plurality of different gas analytes of interest for the second combustible gas sensor, the second electronic circuitry being configured to determine a species of at least one of the plurality of different gas analytes of interest for the second combustible gas sensor from a first output of the second combustible gas sensor during an ON time within a cycle duration of the second combustible gas sensor as the temperature of the second sensing element is increasing and the second electronic circuitry is further configured to determine a concentration of the species of the at least one of the plurality of different gas analytes of interest for the second combustible gas sensor from a second output of the second combustible gas sensor.

* * * * *

UNITED STATES PATENT AND TRADEMARK OFFICE
CERTIFICATE OF CORRECTION

PATENT NO. : 10,234,412 B2
APPLICATION NO. : 15/343956
DATED : March 19, 2019
INVENTOR(S) : Meghan E. Swanson and Michael Alvin Brown It is certified that error appears in the above-identified patent and that said Letters Patent is hereby corrected as shown below:

In the Claims

Column 14, Claim 20, Line 32, delete "gas analytes" and insert --plurality of different gas analytes--.
Column 16, Claim 25, Line 5, delete "to and configured" and insert --and configured to--.

Signed and Sealed this
Eighteenth Day of June, 2019

Andrei Iancu
*Director of the United States Patent and Trademark Office*